United States Patent [19]

Hodgen

[11] Patent Number: 4,845,077
[45] Date of Patent: Jul. 4, 1989

[54] METHOD OF INDUCING OVULATION

[75] Inventor: Gary D. Hodgen, Potomac, Md.

[73] Assignee: Serono Laboratories, Inc., Randolph, Mass.

[21] Appl. No.: 71,521

[22] Filed: Jul. 9, 1987

Related U.S. Application Data

[63] Continuation of Ser. No. 757,202, Jul. 22, 1985, abandoned, which is a continuation of Ser. No. 596,384, Apr. 3, 1984, abandoned.

[51] Int. Cl.$^4$ ............................................. A61K 37/38
[52] U.S. Cl. ........................................ 514/2; 514/15; 514/21
[58] Field of Search ............... 514/2, 15, 21; 530/313, 530/398

[56] References Cited

U.S. PATENT DOCUMENTS 4,317,815  3/1982  Coy et al. ............................. 514/15
4,481,139  11/1984  Folkers et al. ....................... 514/15

OTHER PUBLICATIONS

Yen, Fertil. Steril. Vol. 39, No. 3, Mar. 1983, pp. 257–266.
Fleming et al, The Lancet, Feb. 18, 1984, p. 399.
Ory, Fertil. Steril., vol. 39, No. 5, May 1983, pp. 577–591.
Bergfeld et al, cited in Chem. Abstracts, vol. 87:178225m, 1977.
Dukelow, "Captive Breeding . . ." in Current Therapy in Theriogenology, David A. Morrow, 1980, pp. 1142–1150.
Elsden et al, cited in Chem. Abstracts, vol. 88:131270c, 1978.
Schenken et al, cited in Chem. Abstracts, vol. 100:203981b, 1984.
Bergfeld et al, cited in Chem. Abstracts, vol. 88:164670m, 1978.
Whyte, cited in Chem. Abstracts, vol. 87:194578j, 1977.

*Primary Examiner*—Johnnie R. Brown
*Assistant Examiner*—Jacqueline M. Stone
*Attorney, Agent, or Firm*—Ostrolenk, Faber, Gerb & Soffen

[57] ABSTRACT

A method of inducing ovulation by administering exogenous human menopausal gonadotropins employs FSH as the exogenous human menopausal gonadotripin in the absence of exogenous LH, preferably in conjunction with a gonadotropin releasing factor antagonist. One particular application of the method is in vitro fertilization.

18 Claims, 3 Drawing Sheets

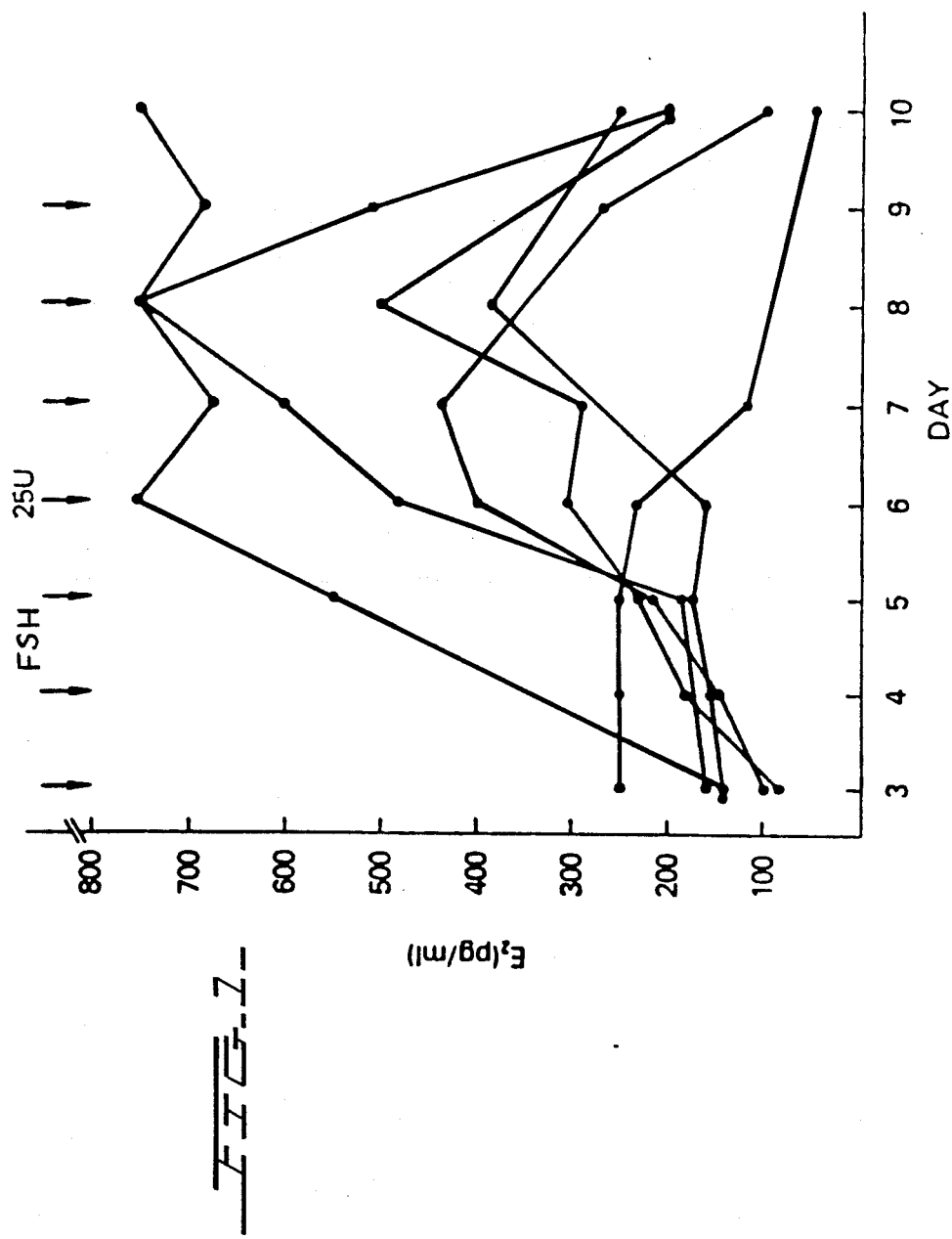
FIG.-1-

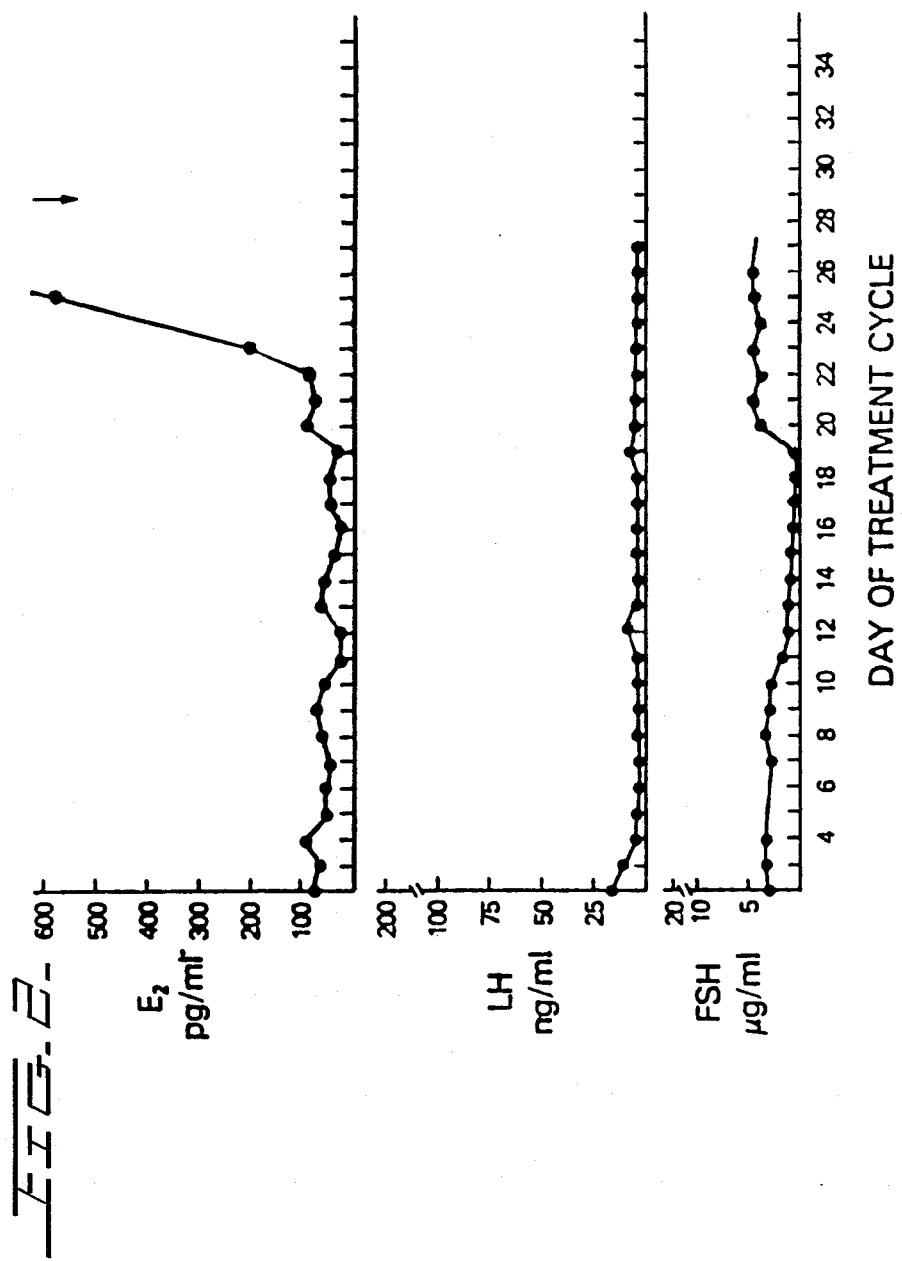

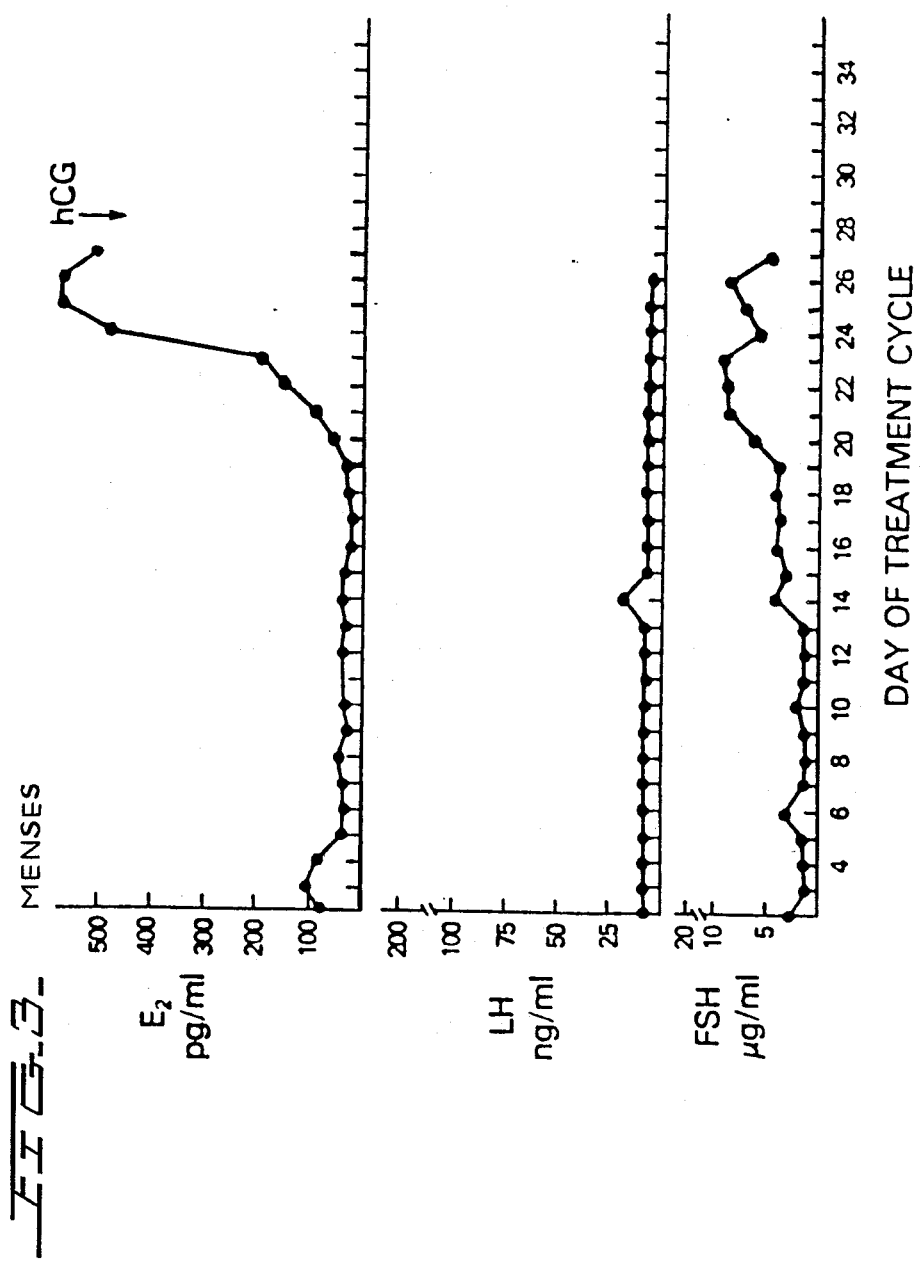

METHOD OF INDUCING OVULATION

This is a continuation of application Ser. No. 757,202 filed July 22, 1985, now abandoned, which was a continuation of application Ser. No. 596,384, filed Apr. 3, 1984 and now abandoned.

BACKGROUND OF THE INVENTION

It is accepted dogma that typically ovulation of a single, fertilizable ovum each menstrual cycle completes a course of oogenesis that began during fetal development. It is not known, however, why from among the thousands of follicles present from birth, only a relative few are recruited each cycle to grow while at the same time others remain at rest. It is also not known why from the host of follicles maturing in each ovary, typically only a single follicle escapes atresia and is selected to ovulate each cycle. Since the vast majority of follicles fall victim to artresia (greater than 99%), understanding the selection of the follicle destined to ovulate is frought with the inherent difficulty of studying the rare exception rather than the predominant rule. One must be extremely careful to distinguish follicle growth that culminates in ovulation (gametogenic follicle growth) from that ending in atresia.

The latter stages of oogenesis in adults (i.e. folliculogenesis) are known to depend, to a large degree, on a complex interplay of hormones from the hypothalamus, pituitary and ovary. However, even though much more is understood about these endocrine relationships today, what determines the fate of an individual follicle remains largely unknown. Since in higher primates both ovaries are functional, the maturation of a single follicle with the potential to ovulate brings with it the obvious concomitant of one active and one quiescent ovary each cycle. It is not knonw how just a single follicle matures to ovulation on only one ovary each cycle, even though both ovaries are perfused by a common systemic circulation.

Three glycoprotein hormones, (luteinizing hormone (or LH), follicle stimulating hormone (or FSH) and human chorionic gonadotropin (or hCG) act on the ovary to stimulate steroid synthesis and secretion. LH and FSH are secreted by the pituitary and together play a central role in regulating the menstrual cycle and ovulation. hCG is secreted by the developing placenta from the early stages of of pregnancy and its role is to maintain steroid secretion by the corpus lutum, which is necessary to prevent ovulation during pregnancy.

In the normal cycle, there is a mid-cycle surge in LH concentration which is followed by ovulation. An elevated estrogen level, which is brought about by the endogenous secretion of LH and FSH, is required for the LH surge to occur. The estrogen mediates a positive feedback mechanism which results in the increased LH secretion.

It is now known how to employ exogenous hormonal stimulation by administering mixed human menopausal gonadotropins, i.e. a combination of FSH and LH, as a prelude to ovulation or follicle aspiration for oocyte collection in in vitro fertilization techniques. Women and monkeys treated with such human menopausal gonadotropins often fail to demonstrate a timely LH surge despite serum estradiol levels sufficient to elicit positive feedback of LH secretion. It has been concluded that the human menopausal gonadotropins stimulate the production of an ovarian factor or factors which blocks the pituitary LH response to the gonadotropin releasing hormone (GnRH). This blockage of GnRH action on the pituitary may be the mechanism by which the human memopausal gonadotropin stimulation prevents the estrogen mediated positive feedback of LH secretion. Non-human primates have been employed in research because of their extensive mimicry of many anatomic, functional and temporal characteristics of the hypothalamic-pituitary-ovarian-uterine axis in women. The individual variation in serum estrogen levels of endocrine normal individuals in response to human menopausal gonadotropin stimulation, as seen in these primates, is well recognized clinically. This has resulted in the adoption of an individualized regimen for ovulation induction by human menopausal gonadotropin/hCG. Although LH surges do occur spontaneously, their appearance is sufficiently infrequent that hCG is routinely administered to induce ovulation.

Administration of human menopausal gonadotropins to ovulatory monkeys produces familiar bilateral ovarian hyperstimulation with attendant superphysiologic elevations of circulating estradiol. Despite these elevated estrogen levels, the monkeys failed to manifest timely gonadotropin responses to estrogen positive feedback, i.e., stereotypically these normal, intact, cycling primates do not have the expected mid-cycle like LH surges despite escalating levels of serum estradiol that usually exceed 400 pg/ml during 12 days of human menopausal gonadotropin therapy. An absence of spontaneous LH surges has also been observed when human menopausal gonadotropin induced ovarian hyperstimulation occurs in post-partum monkeys. These observations fit with the frequent clinical finding that when endocrinologically normal patients are given human menopausal gonadotropins to increase the number of follicles/ova available for in vitro fertilization and embryo transfer therapy, hCG is usually required for the final maturation of these follicles.

It is well established that the appropriate application of mixed exogenous gonadotropins has proved efficacious for ovulation induction or for multiple egg retrieval during in vitro fertilization therapy in women. However, ovarian stimulation through exogenous gonadotropins for in vivo and in vitro fertilization therapy is notoriously difficult to manage and the lack of uniform success with conventional human menopausal gonadotropin medications, those containing FSH and LH in nearly equal amounts, is widely appreciated. Individual responses to human menopausal gonadotropins vary markedly, thereby complicating patient management even when the most flexible (individualized) protocols are used. FIG. 1 charts serum estrogen levels of normal cycling monkeys who had 25 IU FSH administered intramuscularly daily on days 3 to 9 after the onset of menses and illustrates the marked individual variability in response to the agent.

It is the object of this invention to provide an improved method of incuding ovulation by the administration of exogenous human menopausal gonadotropins which increases the likelihood of more uniform follicular maturation or ovulation and is therefore of particular use in connection with in vivo and in vitro fertilization. This and other objects of the invention will become apparent to those skilled in the art from the following detailed description in which:

FIG. 1 graphs estradiol concentration as a function of the administration of human menopausal gonadotropin.

FIG. 2 charts estradiol, LH and FSH concentration in intact cycling monkeys which have been treated with a GnRH antagonist and by human menopausal gonadotropin therapy.

FIG. 3 graphs estradiol, LH and FSH concentration in intact cycling monkeys to whom a GnRH antagonist and by FSH therapy has been administered.

SUMMARY OF THE INVENTION

This invention relates to the inducing of follicular maturation or ovulation by the administration of FSH in the absence of exogeneous LH and is therefore employed in treating infertility syndrome. Individual variations in estrogen response can be mitigated by the cojoint administration of a GnRH antagonist.

DESCRIPTION OF THE INVENTION

It has been found that the administration of exogeneous FSH in the absence of exogeneous LH is capable of inducing the development of multiple ovarian follicles which are responsive to hCG.

Eleven adult female cynomolgus monkeys (*Macaca fascicularis*) were selected for study based on records indicating regular menstrual cycles. The average body weight for these primates was 4.79±0.86 kg.

Counting the first day of spontaneous menses as cycle day 1, the monkeys were treated with 25 IU (im) of FSH twice daily according to three regimens. Group 1 received injections on cycle days 1-11; Group 2 on cycle days 1-4 and Group 3 on days 8-11. For all monkeys, laparoscopies were performed under ketamine anesthesia, beginning on the first day of FSH treatment and serially every 3 to 5 days thereafter to assess the status of ovarian follicular development. In order to test whether these FSH driven follicles could be ovulated, monkeys in Group 1 only received 1,000 IU (im) of hCG on day 12 and retrograde lavage of the fallopian tubes for egg collection 72 hours after hCG treatment was employed to determine whether ovulation had acutally occurred. Daily femoral blood samples were collected beginning on day 1 of the cycle and continued for 40 days or until menstruation. Sera were frozen until radioimmunoassay of LH, FSH, $17\beta$—estradiol and progesterone.

The injections of FSH on cycle days 1-11 induced dramatic and sustained elevations in serum FSH (about 15 ug/ml) and estradiol (about 500 pg/ml). Concurrently, ovarian hyperstimulation was manifested by obvious multiple follicular growth (10-15 prominent follicles by cycle day 8-11). Prior to hCG treatment, serum LH and progesterone remained at basal levels. Within 48 hours after HCG treatment, 1-3 ovulatory stigma were observed on each ovary. Mean serum progesterone and estradiol levels exceed 15 ng/ml and 400 pg/ml, respectively, in mid-luteal phase, indicative of the collective secretory actions of multiple corpora lutea. That ovulation had actually occurred was indicated by the recovery of one or more eggs from the fallopian tubes of each female.

The monkeys treated with FSH during only the early follicular phase of the menstrual cycle demonstrated a prompt increase in serum FSH concentrations (mostly exogeneous) with mean levels near 15 ug/ml on day 4. On discontinuation of FSH injections, circulating FSH levels declined precipitously, below the limits of detection in radio-immunoassay (cycle days 8-11). Serum estradiol levels increased in parallel with the initial increase in circulating FSH, with mean peak values exceeding 300 pg/ml on cycle days 4-6 but even so, no LH surges were observed. Serum progesterone levels remained basal until the onset of the luteal phase in the subsequent spontaneous ovulatory cycle (day 24±2.4). Laparoscopy prior to FSH treatment reveal no advanced follicular development, while on cycle day 5, both ovaries were enlarged with multiple vasicular follicles. Following withdrawal of FSH treatment, the ovaries gradually returned to normal size over the subsequent week. No ovulatory stigma appeared.

Brief administration of FSH on cycle days 8-11 increased serum FSH levels similar to those found in Groups 1 and 2. Mean serum estradiol concentrations increased abruptly, but a spontaneous LH surge was present in only one of four monkeys. The follicular phase serum hormonal profiles for the solitary female were indistinguishable from those of an untreated ovulatory cycle.

The foregoing results show that FSH can be administered alone to enhance the natural ovarian cycle.

In order to decrease the marked individual variability in response to human menopausal gonadotropin therapy, a gonadotropin releasing hormone antagonist is administered in order to eliminate endogeneous pituitary FSH and LH secretion. Typical GnRH antagonists are described in Rees et al, J. Med. Chem., 17, 1016 (1974), Coy et al, Peptides 1976 (Loffed Ed., Editions de L'Universite de Bruxelle 1977) p. 463, Beattie et al, J. Med. Chem., 18, 1247 (1975), Channabasavaiah et al, Biochem. Biophys. Res. Commun., 86, 1266 (1979) and U.S. Pat. Nos. 4,317,815 and 4,431,635, and include (Ac-pClPhe$^1$, pClPhe$^2$, DTrp$^3$, DArg$^6$, DAla$^{10}$)GnRH HCl, [D-Phe$^2$]-LHRH, [D-Phe$^2$, D-Phe$^6$]-LHRH, [D-Phe$^2$, Phe$^3$, D-Phe$^6$]-LHRH, [D-Phe$^2$, D-Trp$^3$, D-Phe$^6$]-LHRH, [D-p-F-Phe-D-Ala$^6$]-LHRH, and [Ac-D-Phe$^1$, D-Phe$^2$, D-Trp$^{3,6}$]-LHRH.

The GnRH antagonist (Ac-pClPhe$^1$,pClPhe$^2$, DTrp$^3$, DArg$^6$, DAla$^{10}$)GnRH HCl, was administered to 20 normal cynomolgus monkeys (1.0 mg/kg/day) in order to eliminate endogeneous pituitary FSH and LH secretion. Superimposed on this treatment, 15 of the monkeys were administered a human menopausal gonadotropin preparation containing approximately equal amounts of FSH and LH and five monkeys were administered FSH only to stimulate ovarian follicular maturation. Control groups received either the combined exogeneous gonadotropins or FSH only (15 monkeys each group). All of the groups received a fixed regimen of gonadotropin therapy for seven consecutive days (25 IU/day/im, cycle days 3-9) followed by hCG (1,000 IU/im) on cycle day 10.

It was observed that the variability in response to gonadotropin treatment was less in the group treated with the GnRH antagonist. The patterns of estradiol rise in serum and the appearance of the ovaries at laparotomy were more uniform when the endogeneous gonadotropin secretion was suppressed. FIGS. 2 and 3 show assay results. While both treatments suppressed the estrogen variability, only the regimen employing the GnRH antagonist and FSH in the absence of LH promoted maturation of multiple ovarian follicles and these follicles were ovulated by hCG with subsequent recovery of two-cell embryos. This is the first time that ovarian follicular maturation has been demonstrated to be promoted by FSH in the absence of detectable levels of LH in serum. Ovulation was also achieved in 9 of the 15 control monkeys treated with only FSH.

The same quantities of FSH can be employed as is employed in the conventional exogenous FSH/LH combinations. Generally, the amount of FSH administered daily to a woman being treated will be in the range of about 75-225 IU and preferably in the range of about 1.5-4.0 IU/kg/day. Intramuscular injection can be employed.

The GnRH antagonist is administered in an amount which is sufficient to suppress endogenous gonadotropin secretion. In general, the average daily dosage will be in the range of about 1.0-3.0 mg per kg and preferably in the range of about 1.5-2.5 mg/kg. Intramuscular injection can be employed. The amount of the antagonist and FSH will best be determined by the attending clinician for the individual being treated. This is particularly true for the GnRH antagonist since the various analogs have different potencies.

Various changes and modifications can be made in the process of this invention without departing from the spirit and scope thereof. The various embodiments which have been described herein were for the purpose of further illustrating the invention, but were not intended to limit it.

What is claimed is:

1. In the method of inducing gametogenic follicle growth by parentally administering exogenous human menopausal gonadotropins which is a combination of FSH and LH in conjunction with human chorionic gonadotropin to a menstruating primate female, the improvement which comprises employing FSH as said exogenous gonadotropin in the absence of exogenous LH and administering a gonadotropin releasing hormone antagonist in an amount sufficient to suppress the endogeneous FSH and LH secretion of said female cojointly with said FSH.

2. The method of claim 1, wherein the daily amount of FSH is about 75-225 I.U.

3. The method of claim 2, wherein the daily amount of FSH is about 1.5-4.0 I.U./kg.

4. The method of claim 1, wherein the ovulated follicles collected.

5. The method of claim 1, wherein the daily amount of the gonadotropin releasing hormone antagonist is about 1.0-3.0 mg/kg.

6. The method of claim 1, wherein the daily amount of the gonadotropin releasing hormone antagonist is about 1.5-2.5 mg/kg and the FSH is about 1.5-4.0 I.U./kg.

7. The method of claim 1, wherein the gonadotropin releasing hormone antagonist is (Ac-pClPhe$^1$, pClPhe$^2$, DTrp$^3$, DArg$^6$, DAla$^{10}$)GnRH HCl.

8. In the method of in vitro fertilization in which ovulation is induced by parenterally administering exogeneous human menopausal gonadotropins which is a combination of FSH and LH to an endocrinologically normal human female in conjunction with human chorionic gonadotropin and the ova realized thereby are collected, the improvement which comprises administering FSH as said exogenous gonadotropin in the absence of exogenous LH co-jointly with a gonadotropin releasing hormone antagonist in an amount sufficient to suppress the endogeneous FSH and LH secretion of said female.

9. The method of claim 8, wherein the daily amount of FSH is about 75-225/I.U.

10. The method of claim 9, wherein the daily amount of gonadotropin releasing hormone antagonist is about 1.0-4.0 mg/kg.

11. The method of claim 8, wherein the daily amount of the gonadotropin releasing hormone antagonist is about 1.5-2.5 mg/kg and the FSH is about 1.5-4.0 I.U./kg.

12. The method of claim 10, wherein the gonadotropin releasing hormone antagonist is (Ac-pClPhe$^1$, pClPhe$^2$, DTrp$^3$, DArg$^6$, DAla$^{10}$)GnRH HCl.

13. A method of suppressing estrogen variability in response to gonadotropin treatment in a primate female which comprises the step of administering a gonadotropin-releasing hormone antagonist in an amount sufficient to suppress the endogenous FSH and LH secretion of said female cojointly with said gonadotropin treatment.

14. The method of claim 13 wherein the gonadotropin treatment comprises administration of a gonadotropin preparation consisting essentially of either (a) FSH alone or (b) FSH and LH in combination.

15. The method of claim 14 wherein the preparation is (b) and contains approximately equal I.U. amounts of FSH and LH.

16. The method of claim 14 comprising the daily administration of about 75 to about 225 I.U. of FSH.

17. The method of claim 14 comprising the daily administration of about 1.5 to about 4.0 I.U./kg FSH.

18. The method of claim 13 wherein the daily administration of about 1.5 to about 4.0 mg/kg FSH.

* * * * *